United States Patent
Bruening et al.

(10) Patent No.: US 11,721,014 B2
(45) Date of Patent: Aug. 8, 2023

(54) METHODS AND SYSTEMS FOR A FIELD-OF-VIEW PREVIEW

(71) Applicant: GE Precision Healthcare LLC, Milwaukee, WI (US)

(72) Inventors: Jan Bruening, Salt Lake City, UT (US); James Romney Clark, Bountiful, UT (US); David White, Holladay, UT (US)

(73) Assignee: GE Precision Healthcare LLC, Milwaukee, WI (US)

( * ) Notice: Subject to any disclaimer, the term of this patent is extended or adjusted under 35 U.S.C. 154(b) by 554 days.

(21) Appl. No.: 16/686,062

(22) Filed: Nov. 15, 2019

(65) Prior Publication Data

US 2021/0150704 A1     May 20, 2021

(51) Int. Cl.
| | |
|---|---|
| A61B 6/00 | (2006.01) |
| G06T 7/00 | (2017.01) |
| G06T 19/00 | (2011.01) |
| G06T 11/00 | (2006.01) |

(52) U.S. Cl.
CPC .......... *G06T 7/0012* (2013.01); *A61B 6/5223* (2013.01); *A61B 6/587* (2013.01); *A61B 6/589* (2013.01); *G06T 11/00* (2013.01); *G06T 19/00* (2013.01); *G06T 2207/10028* (2013.01); *G06T 2207/10116* (2013.01); *G06T 2207/20221* (2013.01)

(58) Field of Classification Search
None
See application file for complete search history.

(56) References Cited

U.S. PATENT DOCUMENTS

| | | | |
|---|---|---|---|
| 5,870,172 | A | 2/1999 | Blume |
| 5,917,882 | A | 6/1999 | Khutoryansky et al. |
| 6,205,347 | B1 | 3/2001 | Morgan et al. |
| 6,768,496 | B2 | 7/2004 | Bieger et al. |
| 7,050,845 | B2 | 5/2006 | Vilsmeier |
| 7,522,701 | B2 | 4/2009 | Jensen et al. |
| 7,725,165 | B2 | 5/2010 | Chen et al. |
| 2012/0170824 | A1 | 7/2012 | Hendriks |
| 2013/0114793 | A1 | 5/2013 | Ohta |

(Continued)

FOREIGN PATENT DOCUMENTS

| | | |
|---|---|---|
| CN | 101627915 A | 1/2010 |
| KR | 20170024560 A | 3/2017 |

(Continued)

OTHER PUBLICATIONS

"Congruence and Beam Perpendicularity," 3H03 Quality Control Website, Available Online at https://qualitycontrolmedradsc3h03.weebly.com/congruence-and-beam-perpendicularity, Mar. 6, 2015, 4 pages.

(Continued)

*Primary Examiner* — Hoon K Song
(74) *Attorney, Agent, or Firm* — McCoy Russell LLP

(57) ABSTRACT

Various methods and systems are provided for a set of devices for an imaging system. In one example, the set of devices includes a first device configured to obtain a first set of image data and a second device configured to obtain a second set of image data along at least one dimension. The first and second sets of data may be compiled to generate a field-of-view (FOV) preview.

18 Claims, 6 Drawing Sheets

(56) References Cited

U.S. PATENT DOCUMENTS

| | | | |
|---|---|---|---|
| 2013/0148779 A1 | 6/2013 | Notohara et al. | |
| 2017/0119329 A1 | 5/2017 | Warner et al. | |
| 2017/0135659 A1 | 5/2017 | Wang et al. | |
| 2017/0224298 A1 | 8/2017 | Hannemann | |
| 2018/0279883 A1* | 10/2018 | Navab | A61B 6/5247 |
| 2020/0268339 A1* | 8/2020 | Hao | A61B 6/0492 |

FOREIGN PATENT DOCUMENTS

| | | |
|---|---|---|
| WO | 2005005381 A2 | 1/2005 |
| WO | 2013063829 A1 | 5/2013 |
| WO | 2016030537 A1 | 3/2016 |
| WO | 2018229286 A1 | 12/2018 |

OTHER PUBLICATIONS

EP application 20206549.6 filed Nov. 9, 2020—Extended Search Report dated Jul. 26, 2021; 7 pages.
KR20170024560—English translation of Abstract; Espacenet—search results, Sep. 17, 2021; 1 page.

* cited by examiner

METHODS AND SYSTEMS FOR A FIELD-OF-VIEW PREVIEW

FIELD

Embodiments of the subject matter disclosed herein relate to x-ray imaging.

BACKGROUND

Radiographic imaging systems may be used in medical and industrial applications as a non-invasive means to obtain images of an inner anatomy of a patient. One example of a medical radiographic imaging system is a mobile fluoroscopy x-ray imaging system which may include an x-ray source positioned at one end of a swing arm. A detector may be positioned at another end of the swing arm. An object, such as a portion of a patient's body, may be inserted in a clearance between the detector and the source, allowing the object to be irradiated. X-ray radiation is captured by the detector after penetrating through the object, enabling generation of an image.

A field-of-view (FOV) of the mobile fluoroscopy x-ray imaging system may be an area of the patient irradiated by an x-ray beam when the patient is positioned between the source and the detector. A size of the FOV may vary based on a distance of the irradiated object from the x-ray source due to divergence of the x-ray beam away from the x-ray source. As the FOV may be varied frequently, e.g., between operations or within one operation, generating an accurate preview of the FOV is desirable.

BRIEF DESCRIPTION

In one embodiment, a method for an imaging system comprises generating a first set of multi-dimensional imaging data, generating a second set of data along at least one dimension, and generating a field-of-view (FOV) preview based on a compilation of the first set of data and the second set of data. In this way a FOV preview may be generated without irradiating a patient.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
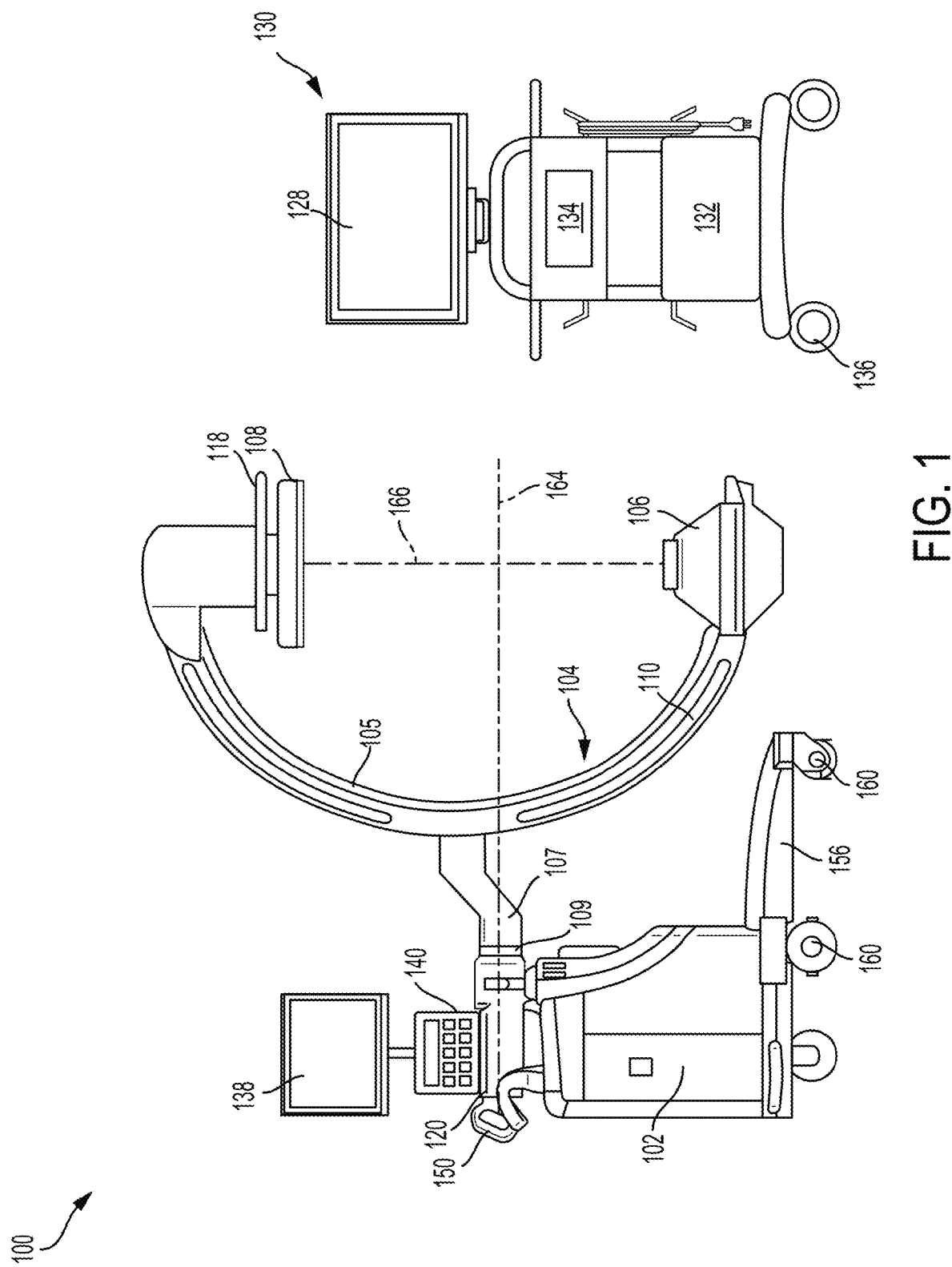
FIG. 1 shows an example of a mobile x-ray imaging system.
Figure 4:
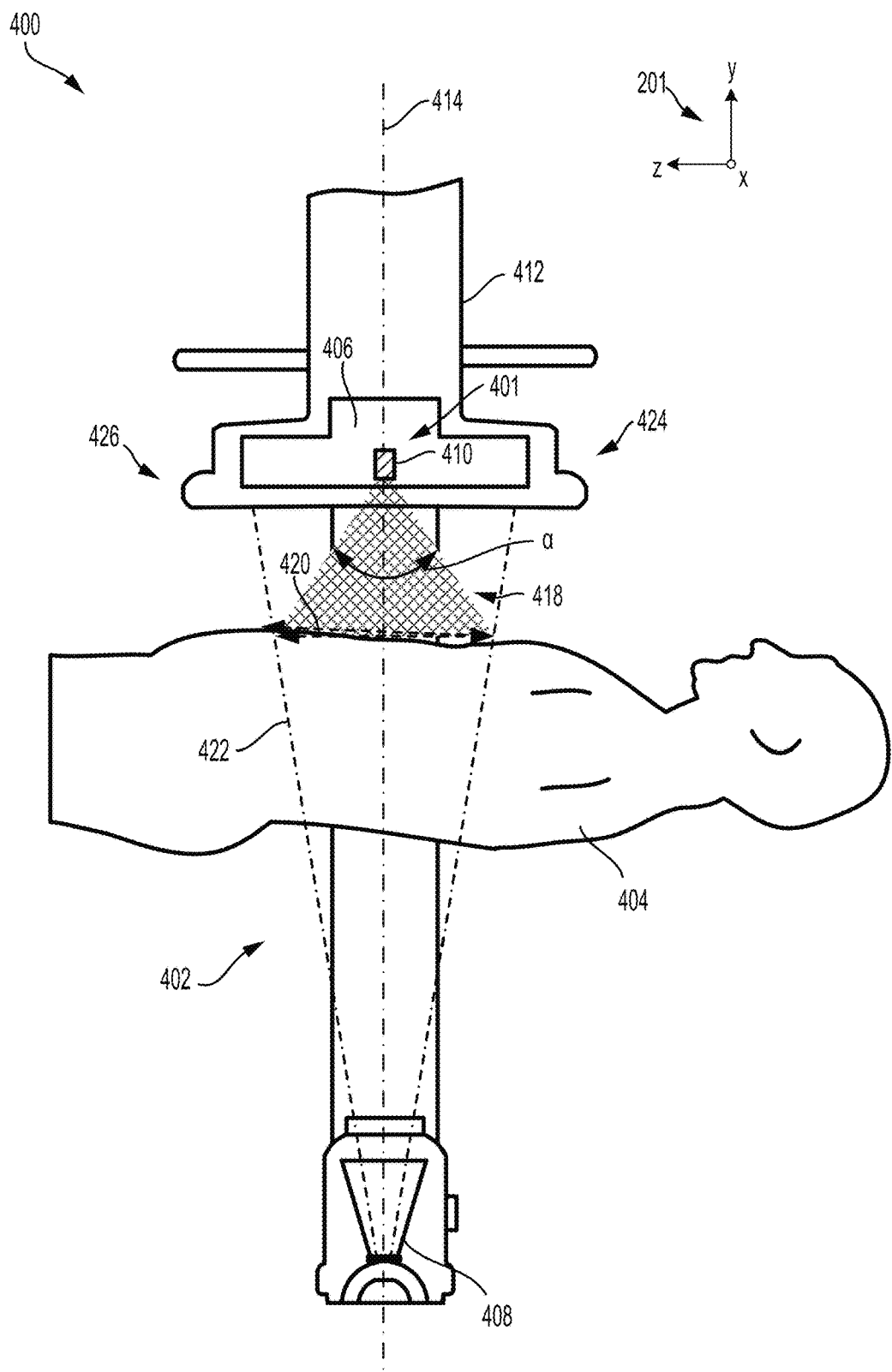
FIG. 4 shows a first view of a mobile arm of a mobile x-ray imaging system with a patient positioned between an x-ray source and a detector of the mobile arm.
Figure 5:
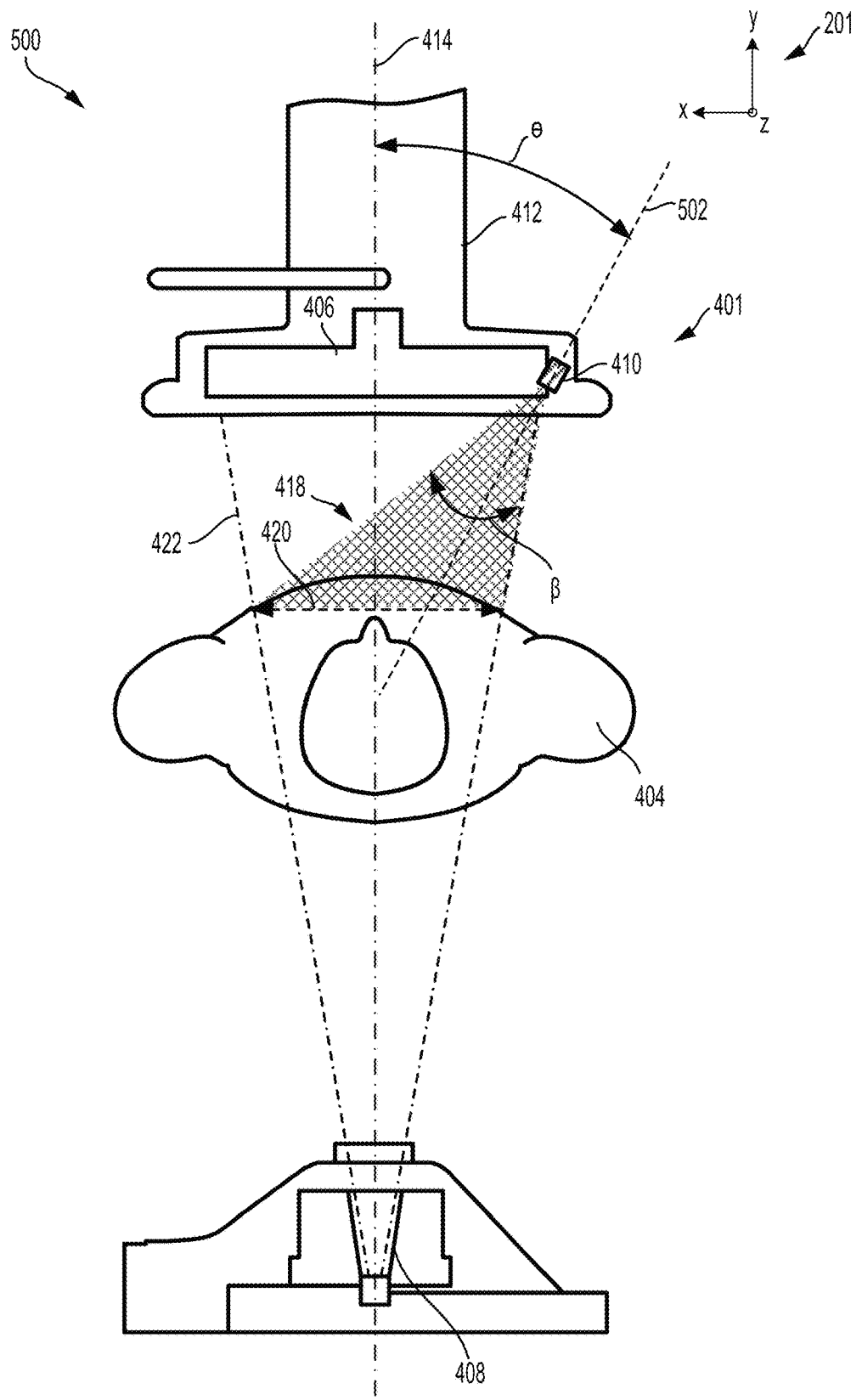
FIG. 5 shows a second view of the mobile arm of the mobile x-ray imaging system with the patient positioned between the x-ray source and the detector of the mobile arm.
Figure 6:
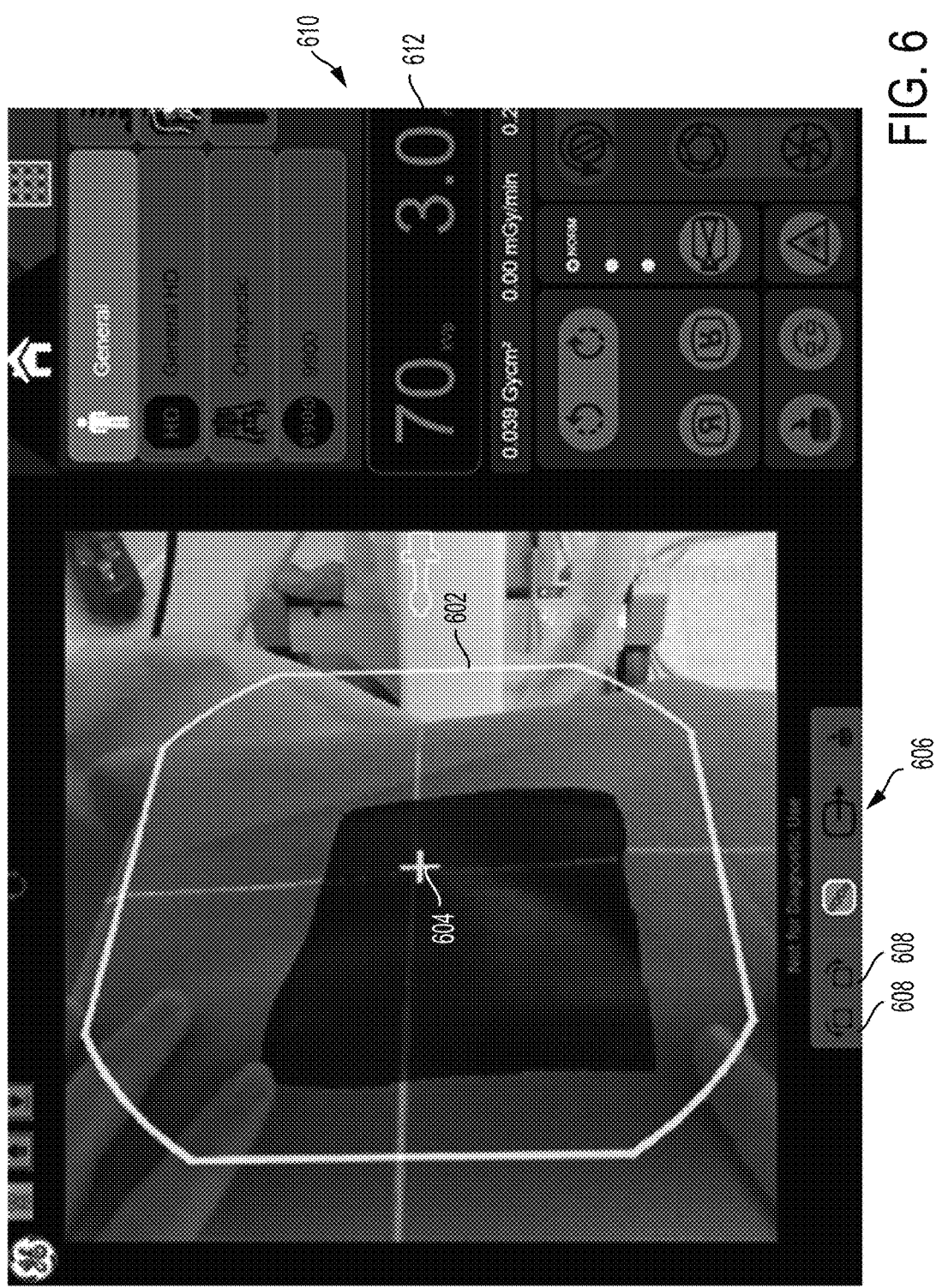
FIG. 6 shows an example of an x-ray FOV preview which may be displayed on a display monitor.
Figure 7:
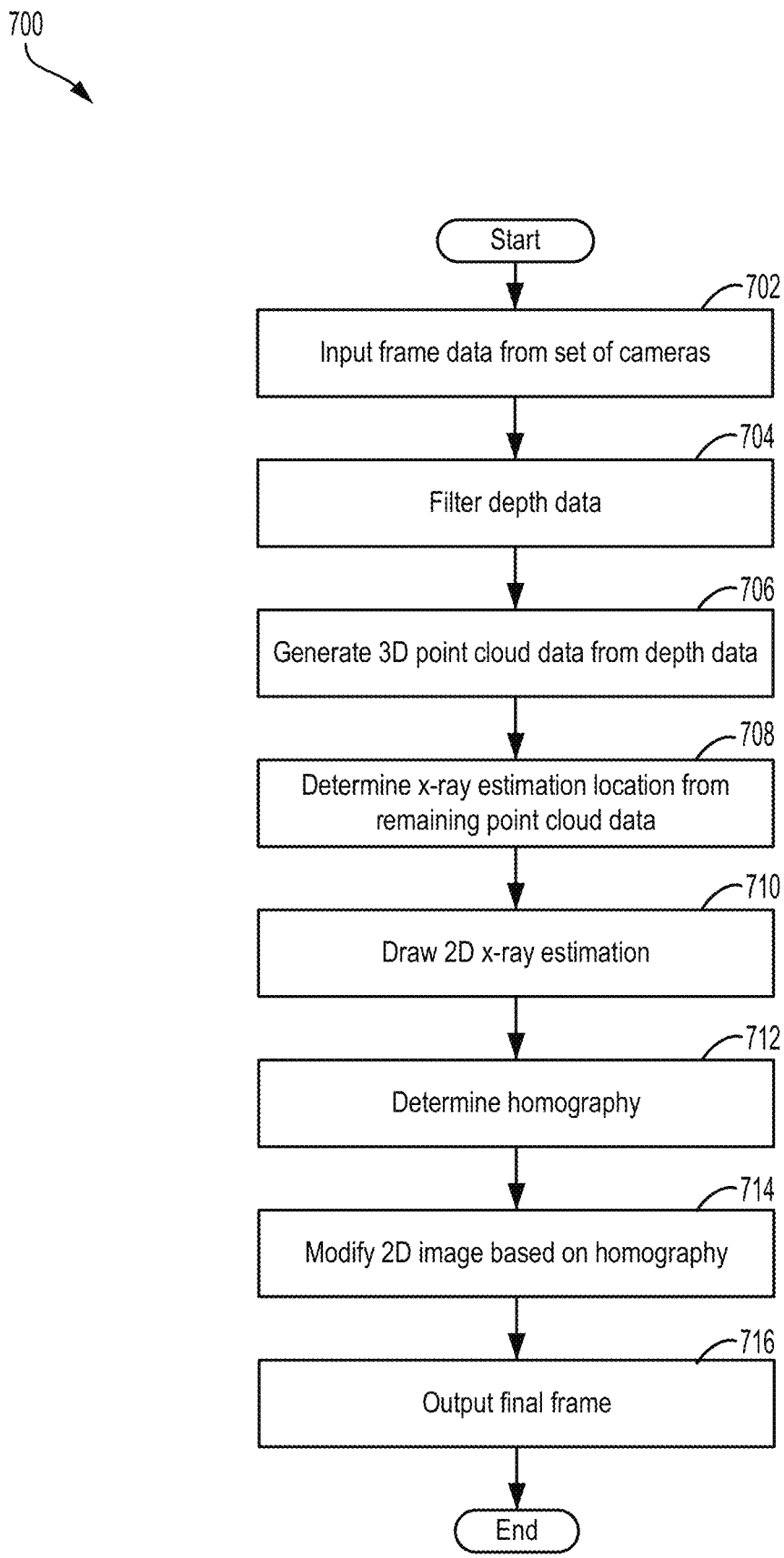
FIG. 7 shows a method for processing data provided by a set of cameras to generate an x-ray FOV preview.

The following description relates to various embodiments of a system for generating a FOV preview for medical imaging. The system may be included in an imaging system, such as a mobile fluoroscopy system as depicted in FIG. 1, to provide a representation of a size and shape of an x-ray FOV. Generating the FOV preview may include projecting an illuminated outline of the FOV onto a patient and/or displaying an image of the FOV on a display device, such as a monitor. The system may include a set of devices mounted adjacent to a detector of the imaging system, a positioning of the set of devices indicated in FIGS. 2 and 3. In some examples, the set of devices may be a set of cameras. The set of cameras may be oriented at specific angles to provide images that may be compiled to infer a complete x-ray FOV preview which may be displayed at the display device. Inclination and FOVs of the set of cameras are shown in FIGS. 4 and 5 and an example of an x-ray FOV preview which may be displayed on a display monitor to an operator and/or surgeon is depicted in FIG. 6. A method for combining three-dimensional and two-dimensional data obtained via the set of cameras into a final frame that accurately depicts the x-ray FOV is shown in FIG. 7.

FIGS. 1-6 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

Mobile fluoroscopy systems may utilize lasers to generate a visible x-ray beam center point on a patient positioned between a detector and a source of the system. The visible center point may be for example, a set of crosshairs projected from the detector side of a mobile arm, providing a guide for positioning the patient relative to an x-ray source prior to obtaining x-ray images of a target portion of the patient's anatomy. While the visible center point identifies a center of an x-ray beam emitted from the source, an area of the x-ray beam, e.g., a size of the beam relative to an irradiated surface, is not indicated.

The area of the x-ray beam may vary depending on a distance of the patient to the x-ray source. The x-ray beam has a diverging, conical shape and as the patient is positioned closer to the source, the beam may become smaller in area, decreasing an x-ray field-of-view (FOV) size and increasing a concentration of x-ray photons irradiating the patient. As the patient is positioned further from the source, the beam may become more diffuse, thereby increasing the FOV size and decreasing patient exposure.

A distance between a point of interest, e.g., a target anatomical region of the patient to be imaged, and a focal spot of the x-ray beam, e.g., a narrowest point of the beam, may be varied if, for example, images from different regions of the patient are desired. The distance may also vary for each patient due to different patient sizes and different anatomical regions to be diagnosed. Relying on the visible center point to adjust a positioning of the patient may not determine whether a sufficient area of the patient will be included in the x-ray to observe the region of interest. To compensate, at least one preliminary x-ray image may be obtained prior to diagnostic imaging to adjust a positioning of the patient relative to the x-ray source. However, preliminary x-ray imaging increases exposure of both the patient and operator(s) to x-ray photons.

In one example, the issue described above may be addressed by a method for generating a preview of an x-ray FOV by generating a video image of an expected beam size and pairing the video image with an image obtained by a stereo camera. The image captured by the stereo camera includes data regarding a distance between an anatomical imaging region and an x-ray detector, a source-to-image distance (SID), and beam collimation size. The data may be used to calculate an expected FOV size and shape and the data may be incorporated into the video image to provide an image displayed on a display device that is representative of the expected FOV.

A painting of the data from the stereo camera onto data from the video image may compensate for distortion and missing data points in the FOV due to surface contours, and other sources of interference, of an imaging region. Without incorporation of the image data by the stereo camera, a resulting FOV preview may provide an inaccurate or incomplete representation of the x-ray FOV. A merging of three-dimensional image data with two-dimensional image data may provide a FOV preview that accurately represents a region of a patient anticipated to be included in an x-ray image. The region may be enclosed within a border with a defined geometric shape. In this way, preliminary x-ray imaging is circumvented and exposure of a patient and operator(s) is reduced. Further details of the method, and a system for generating the FOV preview are provided below, with reference to FIGS. 2-7, following a description of an exemplary mobile fluoroscopy x-ray imaging system.

Turning to FIG. 1, a three-dimensional view of an imaging system 100, having a C-arm 104 with an x-ray source 106 positioned directly below an x-ray detector 108, is disclosed. The imaging system 100 also includes a base unit 102 and a display monitor 134. A base portion 156 of the base unit 102 may include a plurality of wheels 160 that allow the imaging system 100 to be transported from one position to another. Each wheel 160 may include a brake that allows the wheel to be locked into a fixed position, to prevent movement of the imaging system 100.

As shown in FIG. 1, the C-arm 104 may include a C-shaped portion 105 connected to an extended portion 107 coupled to a cross member 120 via a rotatable joint 109. The cross member 120 may be mounted to the base unit 102 which may provide support to the C-arm 104. A lock handle 150 may be adjusted to unlock the C-arm 104, to allow the C-arm to rotate via the rotatable joint 109. As an example, the C-arm 104 may be configured to rotate at least 180 degrees in each direction via the rotatable joint 109 coupling the C-shaped portion 105 to the extended portion 107 of the C-arm 104.

In one example, the C-arm 104 may be rotatable (via the rotatable joint 109) about a central axis 164 of the C-shaped portion 105, to adjust the x-ray source 106 and detector 108 (positioned on opposite ends of the C-shaped portion of the C-arm 104 along a vertical axis 166) through a plurality of positions (e.g., at least switch vertical positions, top and bottom, between the detector and x-ray source). The C-shaped portion 105 of the C-arm 104 may include a plurality of handle bars 110 that may be held when rotating the C-arm via the rotatable joint 109, to adjust positions of the x-ray source 106 and detector 108 before or during operation of the imaging system 100. A curved handle 118, provided on the detector 108, may be used to adjust position of the detector 108 with respect to the x-ray source 106.

During an imaging operation, a portion of a patient's body placed in a clearance (e.g., gap) formed between the x-ray source 106 and detector 108, may be irradiated with radiation from the x-ray source. The radiation may penetrate the portion of the patient's body being irradiated, and travel to the detector 108 where the radiation is captured. By penetrating the portion of the patient's body placed between the x-ray source 106 and detector 108, an image of the patient's body is obtained and relayed to a first display monitor 128 via a connection line (e.g., electrical connection line) where the image is displayed or stored and retrieved later. In one example, the display monitor may display images taken and processed by the imaging system, as they are taken and during the imaging procedure (e.g., in real-time).

The first display monitor 128 may be a separate unit from the C-arm 104 and other components attached to the C-arm 104. The first display monitor 128 may be mounted on a cart 130 that may include a computing unit 132. The computing unit 132 may be communicatively coupled to the first display monitor 128 and may further communicate with a control and computing unit arranged in the base 102 of the imaging system (not shown) via a communication cable or a wireless communication link. The computing unit 132 may be configured to display x-ray FOV previews and x-ray images obtained via the imaging system 100 at the first display monitor 128.

A first input device 134 may be included in the cart 130, used to input commands to control or adjust display of the x-ray images. The first input device 134 may be, for example, a keyboard, a touchpad, a mouse, etc. The cart 130 may be implemented on wheels 136 to allow the cart 130 to be readily repositioned relative to a user and to the C-arm 104. As such, the cart 130 may be positioned next to a surgeon operating on and/or treating a patient. The surgeon's view of the first display monitor 128 may be adjusted as desired by moving the cart 130.

In some examples, the imaging system 100 may include more than one display monitor. For example, a second display monitor 138 may be positioned above the base unit 102. The second display monitor 138 may be fixedly attached to the cross-member 120 and may also display x-ray FOV previews. In some examples, the second display monitor 138 may be configured to show a same display as the first display monitor 138. In other examples, the second display monitor 138 may be positioned to enable an operator of the imaging system 100 to view x-ray FOV previews and resulting x-ray images and manipulate and adjust the view independent of the first display monitor 138. Manipulation and adjustment of images displayed on the second display monitor 138 may be provided by a second input device 140. The second input device may be a tablet device, a keyboard, a mouse, etc.

The base unit 102 may include the control and computing unit that processes instructions or commands sent from the first input device 134 and or the second input device 140 of the imaging system 100 during operation of the imaging system 100. The base unit 102 may also include an internal power source (not shown) that provides electrical power to operate the imaging system 100. Alternatively, the base unit 102 may be connected to an external electrical power source to power the imaging system 100. The x-ray source 106, detector 108, the computing unit 132 in the cart 130, and the control and computing unit in the base unit 102 may communicate via a plurality of connection lines, for example, the plurality of connection lines enabling transmission of instructions and data. In alternative examples, input commands and data may be transmitted between the x-ray source 106, detector 108, and the base unit 102 via a wireless connection or network, thereby advantageously obviating the need for connection lines or cables.

In this way, the imaging system 100 may comprise: the base unit 102; the C-arm 104 coupled to the base unit 102 and including an x-ray source 106 and detector 108 positioned on opposite ends of a C-shaped portion 105 of the C-arm 104; and one or more display monitors, e.g., the first display monitor 128 and the second display monitor 138.

A patient may be positioned on a table within the C-arm, between the x-ray source 106 and the detector 108. As described above, a distance between a target anatomical region of the patient and the x-ray source 106 may affect a size of an x-ray FOV. A FOV preview may be generated by adapting the imaging system with a set of cameras. The FOV preview may include displaying an image of the FOV on one or more display devices, such as the display monitors 128 and 138 of FIG. 1. The set of cameras may include a first camera, configured as a stereo camera, and second camera, configured as a video camera. The first camera may be used to generate a three-dimensional (3D) image of the surface and the second camera may be used to obtain a two-dimensional (2D) video image of a surface of the target anatomical region.

In one example, the first camera may be a binocular infrared camera, positioned directly adjacent to the second camera. The first camera may be configured to provide depth data via infrared imaging combined with predetermined distances between the target anatomical imaging region and an x-ray source, an SID, a collimator iris geometry, etc. In other examples, the first camera may be any other type of stereoscopic camera. In yet other examples, the first camera may not be a camera. Instead, a distance measurement device, such as an ultrasonic range finder, may be paired with the second camera to provide depth data, based on known distancing and geometry of the detector 108, the x-ray source 106, the patient, and the set of cameras.

By positioning the set of cameras together, on a same side of the detector, and similarly inclining both the first camera and the second camera the FOVs of each camera may be similar. As such, the first camera and the second camera may provide image data that is complementary, e.g., the image data is for a same region of the patient, allowing the data from the set of cameras to be matched and compiled. The complementary image data enables image data with different spatial dimensionality, e.g., 3D versus 2D data, to be used together to form a complete and accurate x-ray FOV preview.

Figure 3:
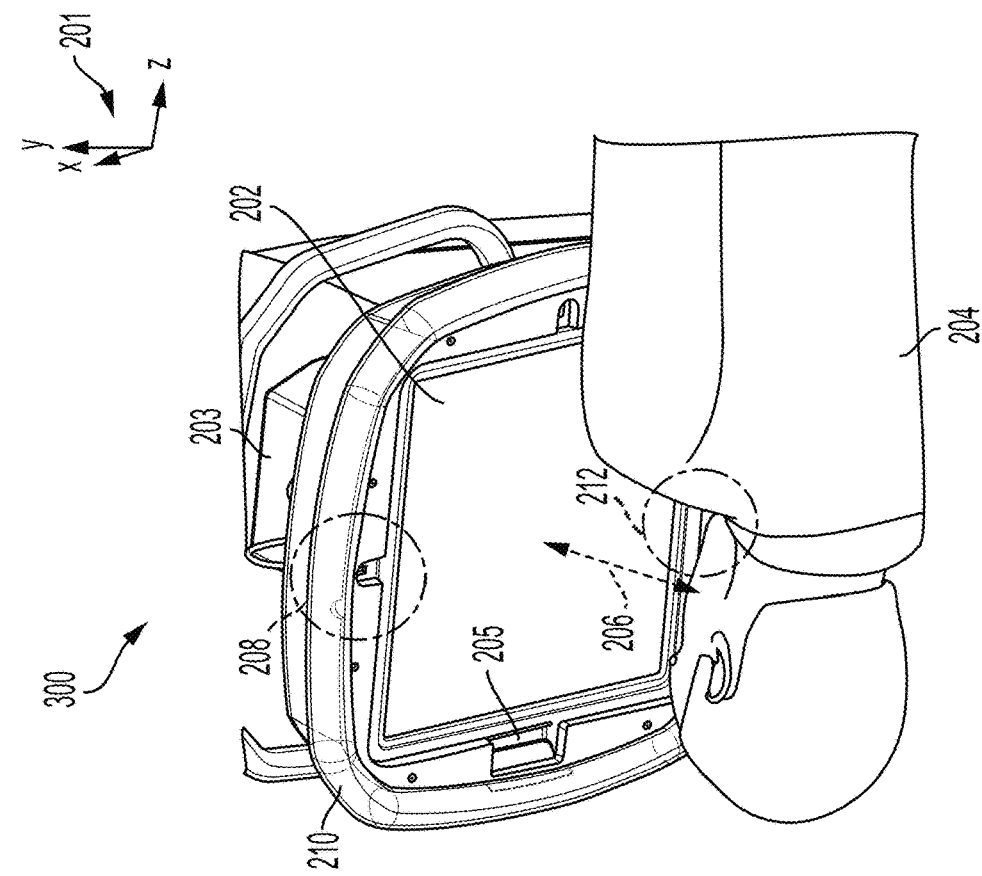
FIG. 3 shows a second perspective view of the detector housing of the mobile x-ray imaging system in which the set of cameras for generating the FOV preview may be embedded.
Figure 2:
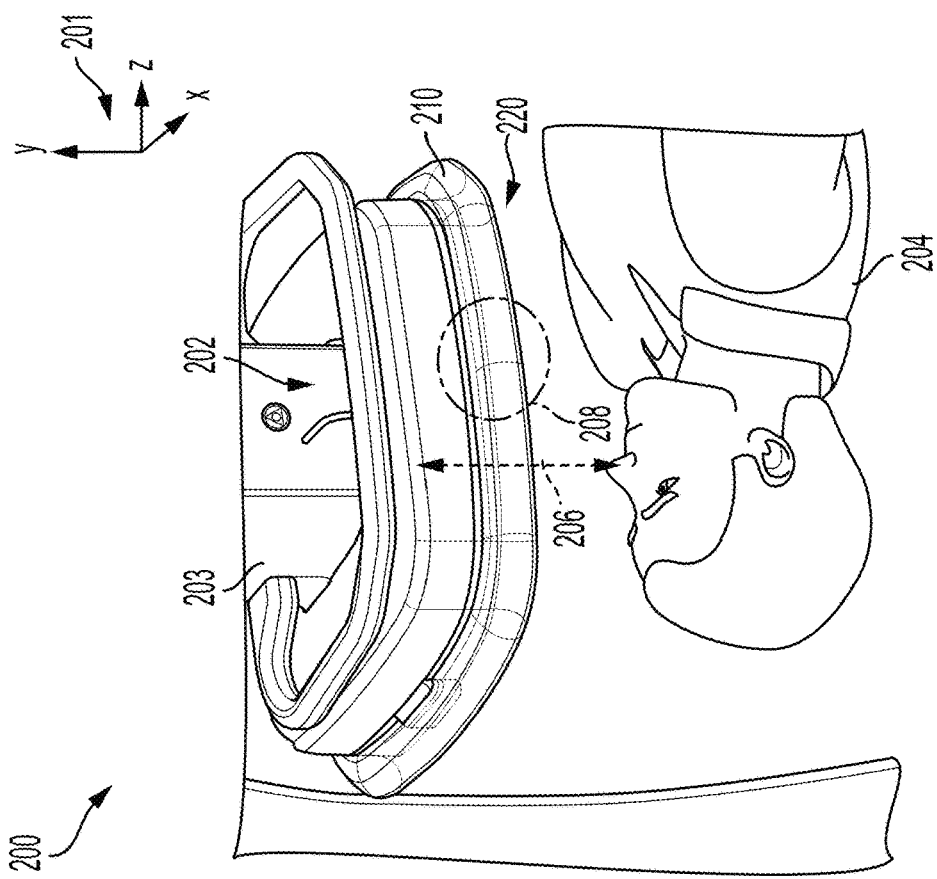
FIG. 2 shows a first perspective view of a detector housing of a mobile x-ray imaging system in which a set of cameras for generating a field-of-view (FOV) preview may be embedded.

The set of cameras may be disposed in an x-ray detector, as shown in a first perspective view 200 and a second perspective view 300 of a detector in FIGS. 2 and 3, respectively. A set of reference axis 201 are provided for comparison between views, indicating an x-axis, a y-axis, and a z-axis. In one example, the y-axis may be parallel with a direction of gravity, the x-axis parallel with a horizontal direction, and the z-axis parallel with a transverse direction. A detector 202 of an x-ray imaging system is shown adjacent to a patient 204 but spaced away from the patient 204 by a distance 206.

The detector 202 may have a flat rectangular area, e.g., a panel, adapted to receive x-ray photons that have passed through the patient 204. A first set of cameras (not shown) may be embedded within a housing 203 of the detector 202, in a region indicated by a first dashed circle 208. The first set of cameras may be mounted at a front side 220 of the detector 202, along a boundary of the detector 202, as indicated by dashed circle 208. A visible light source, such as an infrared laser projector or some other type of light source may be coupled to the first set of cameras, similarly positioning the visible light source along a boundary of the detector 202, at the front side 220. The front side 220 of the detector 202 may be a side of the detector 202 closest to where a surgeon may be positioned during operation of the x-ray imaging system. Thus, mounting the first of cameras adjacent to the surgeon may provide a FOV preview that closely simulates a viewing perspective of the surgeon.

In some examples, the detector 202 may include an additional, second set of cameras. The second set of cameras may be arranged on an opposite side of the detector 202 from the first set of cameras in a region indicated by a second dashed circle 212, as shown in FIG. 3. The second set of cameras may be similarly mounted along the boundary of the detector 202. Both the first and second sets of cameras may face outwards, towards the patient 204 to obtain images of a target anatomical region of the patient 204 irradiated by an x-ray beam. The sets of cameras may therefore be angled specifically to overlap and generate a continuous, cohesive image.

The detector housing 203 may be configured with only the first set of cameras, only the second set of cameras, or with both sets of cameras. When one set of cameras is used, a positioning of the set of cameras may be chosen based on positioning of other components of an imaging system to minimize interference or blockage of the a field-of-view of the set of cameras. Incorporating both sets of cameras may be desirable if excessive angling or inclination of a single set of cameras is demanded, e.g., a greater angle to enable focusing of the set of cameras on a target region than can be accommodated by positioning of the set of cameras within the detector housing 203, or if an incomplete amount of data is provided by the single set of cameras.

In some examples, if a high resolution, accurate representation of an x-ray FOV is not demanded, the set of cameras may include only a stereoscopic camera (e.g., a video camera is not included). As such, the imaging system may be adapted with two stereoscopic cameras, arranged on opposite sides of the detector, and each inclined so that an FOV of each camera is centered on an x-ray FOV passing through the patient.

Inclination of at least one set of cameras in an imaging system is depicted in FIGS. 4 and 5, from a first view 400 in FIG. 4 and a second view 500 in FIG. 5. A mobile arm 402 of an imaging system, such as the C-arm 104 of FIG. 1, is shown in the first view 400 so that a patient 404, positioned between a detector 406 and an x-ray source 408 of the mobile arm 402, is viewed along the y-z plane. The y-z plane, in one example, may be a sagittal plane. In the second view 500, the patient 404 is shown aligned length-wise with the y-x plane, which may, for example, be an axial plane.

A set of cameras 410 may be mounted in a housing 412 of the detector 406. The set of cameras 410, as described above, may include a stereo camera and a video camera to obtain a 3D image and a streaming video image of a target anatomical region of the patient 404. The stereo camera and video camera may be positioned immediately adjacent to one another, aligned along either the z-axis or the x-axis and may be coupled within a single housing.

Within the axial plane, as shown in FIG. 4, the set of cameras 410, e.g., both the stereo camera and the video camera, may be positioned at a front side 401 of the detector 406, where a surgeon may stand. The set of cameras 410 may be aligned with a central axis 414 (and a centerline of the mobile arm 402) and positioned in a central region between a first side 424 and a second side of the 426 of the detector housing 412. A FOV 418 of the set of cameras 410 is depicted as a shaded equilateral triangle in FIG. 4, projected downwards, with respect to the y-axis, and centered along the central axis 414. A size 420 of the FOV 418, as projected onto a top surface of the patient 404, may be similar to a size of an x-ray beam 422 at the top surface of the patient 404, the x-ray beam 422 emitted by the x-ray source 408.

The FOV 418 of the set of cameras 410 may diverge away from the set of cameras 410 with an angle α along the axial plane. In one example, the angle α may be 60 degrees. However, the angle α may vary in other examples, ranging between 40-90 degrees, depending on a spacing and orientation of the stereo camera and video camera relative to one another.

Along the axial plane, as shown in FIG. 5, the set of cameras 410 may be tilted with respect to a central axis 414 of the mobile arm 402. For example, the set of cameras 410 may have an axis 502 inclined at a first angle Θ relative to the central axis 414. In one example, the first angle Θ may be between 30 to 40 degrees. For example, the first angle Θ may be 37 degrees. A field-of-view (FOV) 418, as indicated by a shaded triangular region, of the set of cameras 410 may have a second angle β between 40 to 60 degrees, such as, for example, 50 degrees. As shown in FIGS. 4 and 5, a size 420 of the FOV 418 of the set of cameras 410 projected onto a top surface of the patient 404 may change depending on a distance of the patient 404 from the detector 406.

The set of cameras 410 are positioned along front side 401 of the detector housing 412, adjacent to the detector 406 in FIG. 4. As such, the set of cameras 410 are tilted at the first angle Θ in order to center the FOV 418 within a portion of the patient 404 irradiated by the x-ray beam 422 emitted from the source 408. In other examples, the set of cameras 410 may be instead arranged at a second side 426 of the detector housing 412, opposite of the first side 424. When mounted at the second side 426, the set of cameras 410 may also be inclined at the first angle Θ but from an opposite direction relative to the central axis 414, e.g., tilted by −37 degree with respect to the central axis 414. However, other examples may include the set of cameras 410 tilted at a different angle at the second side 426 than when the set of cameras 410 are located at the first side 424. In yet other examples, the detector housing 412 may include two sets of cameras, positioned at opposite side of the detector 406 and inclined either similarly or differently, so that a FOV of each set of cameras is centered along the x-ray beam 422.

The FOV 418 of the set of cameras 410 may be similar to an x-ray FOV of the imaging system. In other words, an area of the patient 404 that is irradiated and detected to generate an image may be an area encompassed by the FOV 418 of the set of cameras 410. A shape of the FOV, e.g., of both the set of cameras 410 and an x-ray imaging system in which the set of cameras 410 is implemented, when generated by data from the set of cameras 410 and displayed to a user at a display device, may be configured to be a rounded square, or squircle. An example of a display 600 that may be presented to the user on a display device, such as the display monitors 128 and 138 of FIG. 1, is shown in FIG. 6. The display 600 includes a FOV preview 601 on a left side of the display 600, which may be a streaming video image of a surface of a patient.

The FOV preview 601 may show a border 602 outlining a squircle which may be a border of a FOV of a set of cameras included in the imaging system, e.g., the set of cameras 410 of FIGS. 4 and 5. The FOV preview 600 may also include crosshairs 604, also defined by light sources, centered within the border 602. The crosshairs 604 may indicate a center of the FOV preview 600 which may be useful for guiding positioning of a patient relative to the crosshairs 604 to ensure a target anatomical region to be imaged is enclosed by the border 602. In some examples, the border 602 and crosshairs 60 may be illuminated on the patient prior to x-ray imaging in addition to displaying the FOV preview 601.

The border 602 may represent an actual size and shape of an anticipated x-ray FOV, based on a geometry of the set of cameras relative to a source and detector of the imaging system. The FOV preview 601 allows the user to view an area of the patient that is directly irradiated by the x-ray beam and adjust a position of the patient to ensure that a target imaging region is framed within the border 602. The streaming video image may be frequently refreshed and updated, enabling the FOV preview 601 to provide real-time representation of the expected x-ray FOV.

The display 600 may further include various icons and buttons below and to the right of the FOV preview 601 to allow the user to adjust the display 600 as desired. For example, a first set of buttons 606 located below the FOV preview 601 may include buttons 608 for rotating the FOV preview 601 as well as buttons for other adjustments to an orientation of the FOV preview 601. A second set of buttons 610 located to a right of the FOV preview 601 may include, as an example, buttons for selecting display of x-ray parameters, for adjusting the parameters, and for saving the parameters and FOV preview 601 to a database, and for various other modifications to the display 600 and FOV preview 601. A digital display 612 indicating current x-ray parameters may also be shown to the right of the FOV preview 601.

The display 600 may be shown on a first display monitor, such as the display monitor 138 of FIG. 1, positioned adjacent to where an operator, e.g., an x-ray technician, may stand when operating the imaging system. The display 600 allows the operator to adjust a view of the FOV preview 601, e.g., rotating, zooming in/out, etc., as desired. Furthermore, the sets of buttons enables the operator to change operating parameters and display settings. Alternatively or additionally, a display similar to the display 600 may also be shown on a second display monitor, such as the display monitor 128 of FIG. 1, positioned adjacent to a surgeon operating on or diagnosing a patient. The second display monitor may allow the surgeon to adjust a view of the FOV preview independently of the first display monitor, according to the surgeon's preferences. The FOV preview may be turned off/on at the first and second display monitors independently of one another. In some examples, the display shown on the second display monitor may be different from the display 600 of FIG. 6. For example, the display on the second display monitor may show the FOV preview and buttons to adjust the view of the FOV preview but may not include buttons to moderate operating parameters.

As described above, a FOV preview may be generated by data provided via a set of cameras, including a stereo camera and a video camera. Alternatively, the set of cameras may include only the stereo camera, or a distance measuring device combined with the video camera. The data may incorporate geometric data such as distances between an x-ray detector, an x-ray source, a patient, the set of cameras, as well as inclination of the set of cameras. Stereo images obtained from the stereo camera may be used to determine a size of an x-ray FOV, taking both variable x-ray beam collimation and distance from an x-ray detector to a target anatomical region of a patient into account. A stereoscopic depth map of the patient may be created by the stereo images. The video images may be used to display the anticipated FOV without demanding preliminary irradiation of the patient.

By positioning the stereo camera and the video camera together, on a same side of the detector, mapping of the output x-ray FOV preview may be conducted more efficiently, resulting from the similar positioning of both cameras to other components of the imaging system, e.g., the patient, the x-ray source, etc. The cameras may have similar FOVs, thus data from the cameras may be more easily matched. Furthermore, packaging the stereo camera and video together may allow for use of off-the-shelf camera systems with corresponding software.

In one example, the stereo camera may be an off-the-shelf infrared (IR) camera paired with a video camera and configured to provide sufficiently high resolution depth determination even across non-uniform surfaces to generate a complete FOV preview when combined with data from the video camera. The IR information may be combined with a known collimation and distance between the detector and target region of the patient to generate a three-dimensional (3D) depth map. The 3D depth map may be leveraged to clip and scale the video images to a target size based on a known collimator iris or blade position and orientation.

However, curvature in surfaces of the patient may result in gaps in the 3D depth map created by data from the stereo camera. In some instances, a mobile arm of the imaging system may be covered with a transparent, sterile drape. Reflections from the sterile drape may further exacerbate loss of data points in the depth map. Utilization of solely 3D data to generate the FOV preview may result in holes and deformation of the projected FOV preview.

For example, obtaining the FOV preview as an accurate representation of an actual size of the x-ray FOV may be challenging using data from only one type of camera, e.g. the stereo camera. Contours in an imaging region of the patient may lead to wide variations in a projected 2D shape representing a border of the x-ray FOV. In other words, projection of a 2D shape, e.g., a squircle onto a 3D surface, e.g, onto a patient's anatomy, may result in distortion of the 2D shape. The distortion may not allow imaging data from the stereo camera to infer an image of the patient's anatomy to generate the FOV preview.

As an example, when a squircle is projected onto a central region of a chest of the patient, the FOV preview may be relatively intact and complete. An image of the central region of the patient's chest, defined by a border of the FOV preview, may be readily created due to retention of a complete and undistorted outline of the squircle. However, projection of the same squircle on a shoulder region of the patient may result in a highly distorted projected shape that no longer resembles the squircle. Distortion of the squircle may impose difficulties in determining an actual location and size of the x-ray FOV relative to the patient's anatomy. The image data may be missing regions when displayed on a display device or may be so distorted that the FOV preview may not generated or displayed. As a result, preliminary x-ray imaging may be demanded in order to position the patient in desired location relative to the x-ray source, thereby exposing the patient to additional x-ray irradiation.

By matching the 3D data with 2D data provided by the video camera, a method for creating the FOV preview may be highly tolerant of missing depth data from the stereo camera. The 3D data may be lined up with a 2D representation of the FOV, utilizing homography to warp and skew the 3D data to form a complete outline of the FOV preview which may be illuminated onto the patient using visible light. The FOV preview is further displayed on one or more display devices to allow a user to view and manipulate the FOV image(s). Further details of data processing to generate the FOV preview is described below, with reference to FIG. 7.

In one example, projection of 3D data to 2D data is used to project the 3D data back to a plane of the detector which may then be cropped to a size of the FOV. For example, streaming video and depth field data may be collected from the set of cameras. As a first option, the 3D depth map may be used to generate a projection back to a centerline of the detector. The 3D depth map may be missing data, particularly if an imaging surface is uneven or curved. The missing data may be addressed by combining structured illumination, e.g., illuminating a grid or set of lines on the imaging surface with technique for flattening and averaging image data, as described further below.

Alternatively, as a second option, an averaged depth may be used which may produce a flattened mesh at an average distance from the set of cameras to the anatomical imaging region. The second option may be less complex and more continuous than the first option and may be readily used to re-project the video image back to the detector centerline. However, the mesh may introduce a degree of image distortion.

The process for generating the FOV preview described above for a mobile fluoroscopy system may generate a full preview of an expected size, shape, and location of an x-ray beam without demanding preliminary x-ray scanning, unlike conventional mobile fluoroscopy systems which may be configured to only provide crosshairs to indicate a center of the x-ray beam. Patient x-ray dosage is decreased by enabling more accurate initial positioning of the patient relative to the x-ray beam prior to scanning. Furthermore, generation of the FOV preview via the set of cameras allows video images of surgical and medical procedures to be recorded. Additionally, images obtained by the set of cameras may be saved as registration images, allowing navigation back to the same location and positioning of a mobile arm of the mobile fluoroscopy system.

For example, the video image may be saved as a location reference by modifying the image to be a transparent overlay which may be then used as a home position for navigation of the mobile arm. The FOV preview, in addition to the illuminated squircle projected onto the patient, may be displayed on a display device, such as a monitor, as either the transparent overlay, an opaque image, a live image, or a static image, depicting a view of the patient's anatomy within the FOV. The image may be presented on either a left or right monitor when a pair of monitors are included in the mobile fluoroscopy system.

In some examples, when the pair of monitors are included, the FOV preview may be displayed on both monitors, the monitors facing different directions. In this way, a first monitor may be viewed by a surgeon and a second monitor viewed by a technician, for example. The FOV preview may be independently displayed or turned off on either of the first and second monitors. Furthermore, the FOV preview may be rotated as desired by, as an example, a controllable button or icon displayed adjacent to the FOV preview on each of the first and second monitors so that the FOV preview may be aligned with a viewpoint of the surgeon and the technician.

An example of a method 700 for generating an x-ray FOV for an x-ray imaging system is shown in FIG. 7. The imaging system may include a set of cameras, such as the set of cameras 410 of FIGS. 4 and 5, including a first, stereo camera and a second, video camera. The first camera may provide 3D images and may, in some examples, be configured as an infrared camera displaying infrared data. The imaging system may also have a control unit configured with a processor and memory where method 700 may be implemented as executable instructions stored in non-transitory memory of the control unit.

At 702, the method includes receiving depth field data from the set of cameras and generating a displayed frame. A single video and depth frame may be processed to create the displayed frame which includes an estimation of the FOV x-ray based on known (such as pre calibrated) values of a distance from the detector to a patient positioned between the detector and an x-ray source as well as of a beam collimation. The depth field data is filtered at 704 using a spatial and temporal filter to reduce noise and holes while preserving edge information. Outlier data points in the depth field data may be discarded, allowing depth data to be generated via filtering.

At 706, the method includes generating a 3-dimensional (3D) point cloud from the depth data. The depth data is reduced to only points existing on the edges of the x-ray FOV, based on the edge information, to create the 3D point cloud. Remaining 3D point cloud data, e.g., data not at the edge, is evaluated to determine an x-ray depth location from the x-ray detector at 708. The depth location determination may provide an x-ray estimation location closest to the actual distance between the patient and the detector to provide an FOV preview with an accurate representation of a size of the FOV.

The x-ray estimation location may be determined via an algorithm that may vary based on a specific application of the imaging system. For example, a set of data utilizing a maximum size of a coplanar slice of points may be used but other data sets, such as a weighted average depth, may also be used.

At 710, the method includes drawing a 2D x-ray estimation. The 2D x-ray estimation may be a top-down estimation that incorporates all relevant and desirable data such as collimator iris opening, shutter opening and rotation, etc. A homography, e.g., an isomorphism of projective spaces that maps lines to lines, is determined at 712. Points in the point cloud data are matched to known locations in the 2D x-ray FOV estimation location. An open source software library, such as OpenCV, may be used to transform the data to orient an image from the 2D x-ray estimation into a perspective of a frame of a video image provided by the video camera.

The 2D x-ray FOV image, transformed via the open source software library, is modified at 714. Modifying the image includes warping the image using the homography to match the image to the perspective of the video frame. At 716, the method includes blending the warped image into the video frame to output a final display frame. The blending may be repeated for each frame in the video-depth stream. The final display frame may be displayed to a user at a display device, such as a monitor. Furthermore, a shape of the FOV, as well as a center of the FOV, may be projected onto a patient using visible light.

Method 700 may be a dynamic process, allowing the FOV preview to be updated in real-time. For example, method 700 may be calculated at a rate of 30 times per second for a 30 fps video/depth stream provided by the set of cameras, accommodating changes in positioning of the patient, of the detector and x-ray source, in collimator iris size and x-ray source shutters, etc. Thus, the FOV preview continuously provides an accurate representation of an anticipated x-ray beam shape passing through the patient.

In this way, an x-ray FOV preview may be generated without exposing a patient to additional, preliminary irradiation to obtain the preview. The FOV preview may be created based on data from a set of cameras, including a stereo camera and a video camera, configured to provide 3D and 2D information, respectively. The 3D and 2D information may be combined to produce the FOV preview, displayed on at least one display device that represents an actual size and location of the x-ray FOV on the patient. The set of cameras may be mounted adjacent to a detector within a housing of the detector, allowing a known distance between the detector and the patient to be utilized during process of the imaging data.

The technical effect of obtaining an x-ray FOV preview via data provided by a set of cameras, including a stereo camera and a video camera, is that 3D information from the stereo camera is used to generate a depth map which is mapped to a 2D FOV estimation created by information from the video camera to modify the FOV estimation into a representation of the x-ray FOV size and shape. A further technical effect is that the FOV preview provides a representation of an actual geometry and location of the x-ray FOV which may be viewed and adjusted by a user by presenting the FOV preview on at least one display device.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

In one embodiment, a method includes generating a first set of multi-dimensional imaging data, generating a second set of data along at least one dimension, and generating a field-of-view (FOV) preview based on a compilation of the first set of data and the second set of data. In a first example of the method, generating the FOV preview includes projecting the FOV onto a two-dimensional image of a three-dimensional surface of a patient based on the first and second sets of data. A second example of the method optionally includes the first example, and further includes, wherein generating the first set of multi-dimensional imaging data includes obtaining data from a first imaging device and generating the second set of data includes obtaining data from a second imaging device and wherein the first and second imaging devices are positioned in a same region of the imaging system and oriented to have a same imaging FOV as an x-ray FOV. A third example of the method optionally includes one or more of the first and second examples, and further includes displaying the generated FOV preview as an image of a surface of the patient framed within an area of the patient bordered by the illuminated outline on at least one display device. A fourth example of the method optionally includes one or more of the first through third examples, and further includes, wherein displaying the generated FOV preview on at least one display device includes displaying the generated FOV preview on a first monitor adjacent to a technician and on a second monitor adjacent to a surgeon and wherein the displays on the first and second monitors are adjustable independent of one another.

In another embodiment, an imaging system includes a first device configured to obtain a first set of multi-dimensional image data, a second device configured to obtain a second set of image data along at least one dimension, the second set of data complementary to the first set of image data, and a field-of-view (FOV) preview based on a compilation of the first set of data and the second set of data. In a first example of the system, the first device is an infrared imaging camera and the second device is a video camera. A second example of the system optionally includes the first example, and further includes, wherein the first device is a distance measurement device and the second device is a video camera. A third example of the system optionally includes one or more of the first and second examples, and further includes, wherein the set of devices are mounted adjacent to a detector of the imaging system, aimed downwards towards a patient along a same side of the detector along an axial plane, the axial plane aligned perpendicular to a length of the patient arranged prone below the detector and wherein the patient is positioned between the detector and an x-ray source. A fourth example of the system optionally includes one or more of the first through third examples, and further includes, wherein the set of devices are inclined at a first angle relative to a vertical axis of the imaging system and wherein the first angle is configured to center a field-of-view of the set of devices relative to an anticipated x-ray beam passing through the patient. A fifth example of the system optionally includes one or more of the first through fourth examples, and further includes, wherein the set of devices are aligned with the vertical axis and arranged in a central region with respect to the detector along a sagittal plane of the imaging system, the sagittal plane perpendicular to the axial plane. A sixth example of the system optionally includes one or more of the first through fifth examples, and further includes, wherein a size and shape of the FOV preview, as indicated by an illuminated border, is representative of an actual size and shape of an anticipated x-ray beam passing through the patient. A seventh example of the system optionally includes one or more of the first through sixth examples, and further includes, wherein the illuminated border is shown on a display monitor projected onto an image of a surface of the patient to be irradiated by the x-ray beam. An eighth example of the system optionally includes one or more of the first through seventh examples, and further includes, wherein the FOV preview is displayed as an image of an anatomical region of a patient anticipated to be irradiated by an x-ray beam on at least one display device.

In yet another embodiment, a method includes generating a depth map from data provided by a first device of a set of devices, matching the depth map to a field-of-view (FOV) estimation provided by a second device of the set of devices to generate a complete FOV preview, and displaying the complete FOV preview on at least one display device. In a first example of the method, generating the depth map includes obtaining 3-dimensional (3D) image data from the first device and wherein providing the FOV estimation includes obtaining two-dimensional (2D) image data and a video frame from the second device. A second example of the method optionally includes the first example, and further includes, wherein generating the depth map includes using one or more of a known distance from a detector of the imaging system to a patient positioned below the detector, a known distance from the set of devices to the patient, and a collimator iris geometry to create 3D point cloud data. A third example of the method optionally includes one or more of the first and second examples, and further includes, wherein matching the depth data to the FOV estimation includes matching points from the 3D point cloud data to known locations in the FOV estimation via homography to transform the matched data into a perspective of the FOV estimation. A fourth example of the method optionally includes one or more of the first through third examples, and further includes blending the transformed matched data into the video frame to create the complete FOV preview and wherein a region of the patient shown in the FOV image framed by an illuminated border corresponds to an anticipated size and shape of an x-ray beam. A fifth example of the method optionally includes one or more of the first through fourth examples, and further includes, wherein a process for generating the complete FOV preview is repeated for every frame in a video and depth stream provided by the set of devices to continuously update the complete FOV preview.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for an imaging system, comprising:
generating a depth map from data provided by a first device of a set of devices, wherein generating the depth map includes:
obtaining 3-dimensional (3D) image data from the first device; and
using a known distance from a detector of the imaging system to a patient positioned below the detector, a known distance from the set of devices to the patient, and a collimator iris geometry to create 3D point cloud data;
matching the depth map to a field-of-view (FOV) estimation provided by a second device of the set of devices to generate a complete FOV preview; and
displaying the complete FOV preview on at least one display device.

2. The method of claim 1, wherein providing the FOV estimation includes obtaining two-dimensional (2D) image data and a video frame from the second device.

3. The method of claim 1, wherein matching the depth data to the FOV estimation includes matching points from the 3D point cloud data to known locations in the FOV estimation via homography to transform the matched data into a perspective of the FOV estimation.

4. The method of claim 3, further comprising blending the transformed matched data into the video frame to create the complete FOV preview and wherein a region of the patient shown in the FOV image framed by an illuminated border corresponds to an anticipated size and shape of an x-ray beam.

5. The method of claim 1, wherein a process for generating the complete FOV preview is repeated for every frame in a video and depth stream provided by the set of devices to continuously update the complete FOV preview.

6. The method of claim 1, further comprising leveraging the depth map to clip and scale video images to a target size.

7. The method of claim 1, wherein the first device is a stereo camera.

8. The method of claim 1, wherein the first device is an infrared imaging camera.

9. The method of claim 1, wherein the first device is a distance measurement device.

10. The method of claim 1, wherein the second device is a video camera.

11. The method of claim 1, wherein the set of devices are mounted adjacent to a detector of the imaging system, aimed downwards towards a patient along a same side of the detector along an axial plane, the axial plane aligned perpendicular to a length of the patient arranged prone below the detector and wherein the patient is positioned between the detector and an x-ray source.

12. The method of claim 11, wherein the set of devices are inclined at a first angle relative to a vertical axis of the imaging system and wherein the first angle is configured to center a field-of-view of the set of devices relative to an anticipated x-ray beam passing through the patient.

13. The method of claim 12, wherein the set of devices are aligned with the vertical axis and arranged in a central region with respect to the detector along a sagittal plane of the imaging system, the sagittal plane perpendicular to the axial plane.

14. The method of claim 11, wherein a size and shape of the FOV preview, as indicated by an illuminated border, is representative of an actual size and shape of an anticipated x-ray beam passing through the patient.

15. The method of claim 14, further comprising showing the illuminated border on a display monitor projected onto an image of a surface of the patient to be irradiated by the x-ray beam.

16. The method of claim 1, wherein displaying the complete FOV preview on the at least one display device includes displaying the FOV preview as an image of an anatomical region of a patient anticipated to be irradiated by an x-ray beam.

17. The method of claim 1, wherein creating the 3D point cloud data includes reducing depth data to only points at edges of an x-ray FOV based on edge information.

18. The method of claim 17, further comprising evaluating 3D point cloud data not at edges of the x-ray FOV to determine an x-ray depth location from an x-ray detector.

* * * * *